United States Patent
Rovnan et al.

(10) Patent No.: US 12,170,132 B1
(45) Date of Patent: Dec. 17, 2024

(54) SYSTEMS AND METHODS FOR GENERATING ELECTRONIC COMMUNICATIONS AND UPDATING ELECTRONIC DATABASES

(71) Applicant: TeleTracking Technologies, Inc., Pittsburgh, PA (US)

(72) Inventors: John Rovnan, Gibsonia, PA (US); Nathan Mancine, Cranberry Township, PA (US); Katheryn Romano, Wexford, PA (US); Dustin T. Sandrock, Pittsburgh, PA (US); Jason Spector, Pittsburgh, PA (US)

(73) Assignee: TELETRACKING TECHNOLOGIES, INC., Pittsburgh, PA (US)

(*) Notice: Subject to any disclaimer, the term of this patent is extended or adjusted under 35 U.S.C. 154(b) by 199 days.

(21) Appl. No.: 15/395,646

(22) Filed: Dec. 30, 2016

Related U.S. Application Data

(63) Continuation-in-part of application No. 14/974,775, filed on Dec. 18, 2015, now Pat. No. 10,475,535.
(Continued)

(51) Int. Cl.
  *G16H 10/60* (2018.01)
  *G06F 16/23* (2019.01)
  *G06F 16/27* (2019.01)

(52) U.S. Cl.
  CPC .......... *G16H 10/60* (2018.01); *G06F 16/235* (2019.01); *G06F 16/275* (2019.01)

(58) Field of Classification Search
  CPC ........ G06Q 50/22; G06Q 50/24; G16H 10/60; G06F 16/235; G06F 16/275
  See application file for complete search history.

(56) References Cited

U.S. PATENT DOCUMENTS

| | | | |
|---|---|---|---|
| 6,957,188 B1 * | 10/2005 | Dellevi | G06Q 10/063112 705/7.14 |
| 2003/0007628 A1 | 1/2003 | Vortman et al. | |

(Continued)

FOREIGN PATENT DOCUMENTS

| | | | | |
|---|---|---|---|---|
| WO | WO 2013149316 A1 * | 10/2013 | ....... | G06Q 10/06311 |

OTHER PUBLICATIONS

Extended European Search Report for EP Application No. 15201394.2-1952 dated May 9, 2016 (7 pages).

*Primary Examiner* — Eliza A Lam
(74) *Attorney, Agent, or Firm* — FERENCE & ASSOCIATES LLC

(57) ABSTRACT

Systems and methods are disclosed for detecting partial electronic schedule updates and generating targeted electronic notifications. A system may comprise a communication interface configured to establish bidirectional communication with a plurality of electronic devices, and at least one processor. The at least one processor is configured to receive trade request information from a first electronic device, determine a second electronic device associated with the request recipient, generate and transmit a request electronic notification to the second electronic device including at least one response hyperlink, receive, from the second electronic device, acceptance data generated in response to selection of the at least one response hyperlink, automatically modify an electronic record to update schedule information for the request recipient and the requestor, and automatically generate and transmit update electronic notifications to the first and second electronic devices for generating graphical user interfaces reflecting completion of the trade request.

18 Claims, 10 Drawing Sheets

Related U.S. Application Data

(60) Provisional application No. 62/094,682, filed on Dec. 19, 2014.

(56) References Cited

U.S. PATENT DOCUMENTS

| | | | |
|---|---|---|---|
| 2003/0018509 A1* | 1/2003 | Ossip | G06Q 10/06 705/7.16 |
| 2005/0177407 A1* | 8/2005 | Barni | G06Q 10/06 705/7.14 |
| 2006/0053035 A1 | 3/2006 | Eisenberg | |
| 2010/0306017 A1* | 12/2010 | Dreyfuss | G06Q 10/063116 705/7.16 |
| 2011/0153352 A1* | 6/2011 | Semian | G06Q 10/06 705/2 |
| 2012/0290311 A1 | 11/2012 | Tara et al. | |
| 2013/0090968 A1* | 4/2013 | Borza | G06Q 10/06 705/7.16 |
| 2014/0114684 A1* | 4/2014 | Semian | G16H 40/67 705/2 |

\* cited by examiner

| Schedule | ⇨ Sign Out |
|---|---|
| Dr. W (me) | Change |

— TUESDAY, MARCH 29 —

| 8:00 am 12:00 pm | Hospital A Cardiology |
|---|---|
| 12:00 pm 2:00 pm | Hospital B Cardiology |
| 0 pm 0 pm | Hospital B Cardiology | ➚ Trade |

— WEDNESDAY, MARCH 30 —

| 8:00 am 2:00 pm | Hospital A Cardiology |
|---|---|
| 2:00 pm 8:00 pm | Hospital B Cardiology |

On Call     Schedule

SYSTEMS AND METHODS FOR GENERATING ELECTRONIC COMMUNICATIONS AND UPDATING ELECTRONIC DATABASES

CROSS-REFERENCE TO RELATED APPLICATION

This application is a continuation-in-part of U.S. patent application Ser. No. 14/974,775, filed Dec. 18, 2015, which claims the benefit of U.S. Provisional Patent Application No. 62/094,682, filed Dec. 19, 2014. The contents of the above-referenced applications are expressly incorporated herein by reference in their entirety.

TECHNICAL FIELD

The subject matter described herein generally relates to computerized database management, particularly with respect to updating electronic databases, and generating and communicating database updates in a centralized communication system.

BACKGROUND

Many facilities use manual techniques for creating and distributing schedules, such as on-call scheduling for hospital physicians covering various service lines (e.g., cardiology, neurology, orthopedics, etc.). Oftentimes, the on-call schedule is created in a static electronic format such as a spreadsheet, and then posted on an accessible page (e.g., posted to a MICROSOFT SHAREPOINT site). Other times the on-call schedule is faxed or delivered by hand to the clinicians.

Traditional on-call schedule systems are largely static and thus are often incomplete or outdated. For example, original creation of the on-call schedule is not timely updated in traditional systems, and the schedules use minimal and sometimes incorrect information. Furthermore, many current systems do not source up-to-date data from different systems within a facility, and therefore the systems throughout a facility are often out of sync and contain disparate information.

In view of the deficiencies and drawbacks of current systems and the technical problems discussed above, improved systems and methods for automated status update communication and electronic database updates is desired.

SUMMARY

Disclosed embodiments relate to on-call schedule systems in a facility using real-time data collection from one or more associated networked scheduling databases, and employing one or more communication networks to generate and transmit notifications and messages regarding updates associated with collected data. In some embodiments, the facility may include a medical facility, a hotel, or any other type of facility that benefits from accurate and dynamic communication of on-call schedule systems.

Disclosed embodiments address the technical problems discussed above through the use of a centralized server that dynamically and automatically queries networked databases located throughout the facility to obtain real-time data regarding schedule updates. Thus, the disclosed embodiments provide a combination and arrangement of computerized hardware in conjunction with ordered combinations of steps in a particular application. As a result, the disclosed embodiments can reduce inaccurate on-call schedules present in traditional systems and provide a dynamic and accurate way of communicating on-call schedule information.

Consistent with the present embodiments, a centralized communication system for detecting partial electronic schedule updates and generating targeted electronic notifications is disclosed. The system may include a communication interface configured to establish bidirectional communication with a plurality of electronic devices, a memory storing computer-executable instructions, and at least one processor. The at least one processor may be configured to receive, via the communication interface from a first electronic device, trade request information including an identification of a requestor, a request recipient, and shift data, determine a second electronic device associated with the request recipient, generate and transmit a request electronic notification to the second electronic device, the request electronic notification including instructions for generating a graphical user interface including the shift data and at least one response hyperlink, receive, from the second electronic device, acceptance data generated in response to selection of the at least one response hyperlink, automatically modify an electronic record to update schedule information for the request recipient and the requestor, and automatically generate and transmit update electronic notifications to the first and second electronic devices for generating graphical user interfaces reflecting completion of the trade request.

Consistent with the present embodiments, a system is disclosed. The system may comprise a memory storing computer-executable instructions a processor of an electronic device configured to execute the stored instructions to access a list of on-call clinicians, access a digitized list of requirements for a healthcare facility on-call clinician schedule; producing, generate an initial on-call clinician schedule based on the list of on-call clinicians determine whether the list of requirements is satisfied by the initial on-call clinician schedule; and provide an indication as a result of the determining.

Consistent with the present embodiments, a computerized method for detecting partial electronic schedule updates and generating targeted electronic notifications using a centralized communication system is disclosed. The method may comprise receiving, by at least one processor via a communication interface and from a first electronic device, trade request information including an identification of a requestor, a request recipient, and shift data, determining a second electronic device associated with the request recipient, generating and transmit a request electronic notification to the second electronic device, the request electronic notification including instructions for generating a graphical user interface including the shift data and at least one response hyperlink, receiving, from the second electronic device, acceptance data generated in response to selection of the at least one response hyperlink, automatically modifying an electronic record to update schedule information for the request recipient and the requestor, and automatically generating and transmit update electronic notifications to the first and second electronic devices for generating graphical user interfaces reflecting completion of the trade request.

In an embodiment, the list of requirements includes at least one of a clinician scheduling preference, a facility on-call coverage requirement, and a facility scheduling balance preference. An embodiment may determine at least one of the list of requirements is not satisfied and automatically generate at least one modification to the initial on-call clinician schedule based on the list of requirements.

In an embodiment at least one update to the initial on-call clinician schedule is received from an on-call clinician mobile device and an embodiment publishes, based on the at least one update, a revised on-call clinician schedule. The publishing may comprise updating a database maintaining on-call clinician information. The publishing may comprise communicating a message to at least one clinician mobile device. In an embodiment, the at least one update may comprise a temporary unavailability notification, an unavailability notification, or an unavailability preference.

Consistent with the present embodiments, a method is disclosed. The method may comprise receiving, from an on-call clinician mobile device, at least one update to an initial on-call clinician schedule; updating, using a processor, the initial on-call clinician schedule based on the at least one update; and automatically communicating, using a wireless communication network, the at least one update to at least one other clinician mobile device.

In an embodiment, the at least one other clinician mobile device is an on-call clinician mobile device. The at least one update may comprise a temporary unavailability update. The temporary unavailability update may be automatically inferred using at least one device characteristic of the on-call clinician mobile device. The at least one device characteristic may be selected from the group consisting of a real-time location of the on-call clinician mobile device, orientation data of the on-call clinician mobile device, and accelerometer data of the on-call clinician mobile device.

In an embodiment, a database including priority clinician information may be accessed and the on-call clinician mobile device selected using the priority clinician information. The updating may comprise selecting an alternative on-call clinician for an on-call coverage period based on the priority information. The communicating may comprise communicating the update to the on-call clinician mobile device selected using the priority clinician information. The communicating may comprise sending a notification that the alternative on-call clinician is now on-call. The notification may be selected from the group consisting of an SMS text message, an email, a page, and an automated voice call.

Consistent with the present embodiments, a method is disclosed. The method may comprise receiving, at centralized electronic management system, at least one request for on-call clinician schedule data; accessing, using the centralized electronic management system, stored on-call clinician scheduling data based on the at least one request; and communicating, using a wireless communication network, a response to the at least one request for the on-call clinician schedule data; the response comprising at least a currently on-call clinician for a service line indicated by the at least one request.

In an embodiment, the centralized electronic management system responds to at least one request issued from a clinician device. The clinician device may issue the request according to a patient transfer application.

Consistent with the present embodiments, a method is disclosed. The method may comprise accessing, using a centralized electronic management system, stored on-call clinician scheduling data; analyzing, using a processor of the centralized electronic management system, the on-call clinician scheduling data for a service line in a given time frame; and identifying at least one underutilized on-call service line time frame within the given time frame, wherein the at least one underutilized on-call service line is defined according to a user configuration. The method may include generating an adjusted on-call clinician schedule based the identified at least one underutilized on-call service line time frame.

The foregoing is a summary and thus may contain simplifications, generalizations, and omissions of detail; consequently, those skilled in the art will appreciate that the summary is illustrative only and is not intended to be in any way limiting.

For a better understanding of the embodiments, together with other and further features and advantages thereof, reference is made to the following description, taken in conjunction with the accompanying drawings. The scope of the invention will be pointed out in the appended claims.

BRIEF DESCRIPTION OF THE DRAWINGS

FIG. 6 illustrates an exemplary graphical user interface where a user can begin a trading process in accordance with disclosed embodiments.

FIG. 7 illustrates an exemplary graphical user interface where a user can select a recipient and send a trade request in accordance with disclosed embodiments.

FIG. 10 illustrates an exemplary graphical user interface where a user can hide an accepted trade request.

DETAILED DESCRIPTION

Figure 1:
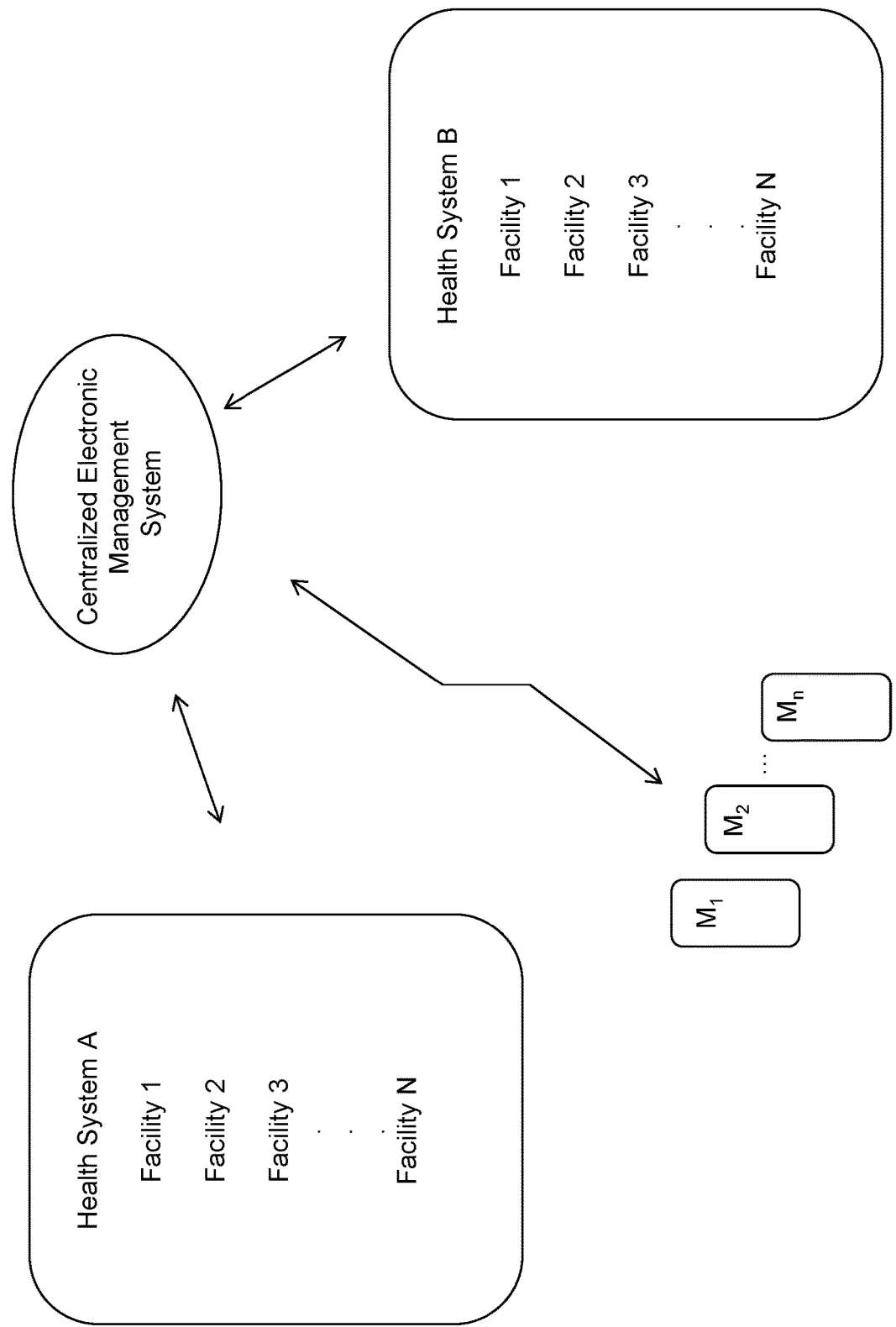
FIG. 1 illustrates an example on-call clinician scheduling system in accordance with disclosed embodiments.

It will be readily understood that the components of the embodiments, as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, the appearance of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, et cetera. In other instances, well known structures, materials, or operations are not shown or described in detail to avoid obfuscation.

Conventional on-call clinician schedules tend to be static documents. For example, a paper calendar schedule is filled out with on-call clinician information for given days and time slots. Even when formatted electronically (e.g., internal web page, general calendaring program or application), the information in the on-call clinician schedule tends to be static, only infrequently updated, if at all. Moreover, using a manual preparation technique renders it difficult to integrate competing interests (e.g., facility requirements for on-call clinicians, clinicians needs or desires, such as scheduling preferences, etc.). Moreover, currently the on-call clinician schedule is not integrated with other data information systems (e.g., patient tracking systems, physician communication systems, real-time location systems, etc.). Thus, there are rich data sources (e.g., real-time location data regarding patients, clinicians, etc.) that are unutilized by current health system data processing systems.

Generally then on-call clinician schedules tend to be prepared using traditional approaches (e.g., paper schedules, manually input data entries into a calendar application, etc.). These approaches lead to a static schedule that on creation is not prepared using the best data available and during use leads to misinformation being given, lengthening patient wait times when an on-call clinician is needed.

Accordingly, disclosed embodiments may be directed to addressing the technological challenge of synchronizing a scheduling database. Also, disclosed embodiments may improve the operation of the scheduling database. For example, by incorporating autonomous real-time location data from patients and clinicians, disclosed embodiments may increase processing efficiency by using light-weight incremental updates, rather than processing a large bulk updates that may be provided in isolated batches. Consistent, regular updates may prevent processing spikes in server load that would otherwise occur when processing bulk schedule updates by handling schedule updates as they occur and by updating selected electronic devices that are associated with the schedule updates, rather than pushing bulk updates at longer intervals and to many additional electronic devices that may not be associated with any of the updates.

An embodiment therefore goes beyond creating and viewing a schedule and addresses the issues that the various users have with conventional on-call clinician scheduling technology. Instead of simply inputting of on-call clinician schedules, an embodiment allows for the tracking of preferences (e.g., clinician time off requests), monitoring of total on-call hours for clinicians (e.g., per week, per month, and per year), and assigning of clinicians to cover multiple facilities. Furthermore, integration with other data systems (e.g., patient tracking, clinician communication, asset tracking, etc.), provides an on-call scheduling system with precise, up to-date-data where and when it is needed, anticipating use instead of simply being a repository of schedules.

An embodiment also allows for the creation of groups that can correspond to any entity desired. Groups for example may be created for units, service lines, hospitals, etc. Once these groups are created, any schedulable individual may be associated with these groups and assigned to cover given time periods. The individuals may be physicians, nurses, physician assistants or any other staff member that needs to be assigned in an on-call role. Time periods are variable and can be set up in regular intervals such as 12 hour or 24 hour shifts as well as fully customizable durations (8 a.m.-5 p.m., etc.).

Acknowledging that it is not just the entering of schedules that is a problem with conventional scheduling systems, an embodiment enables staff to indicate in an electronic and/or automated fashion days unavailable as well as hierarchical communication preferences (e.g., never Saturdays, preference for no Wednesdays, call physician A before physician B, etc.). In order to be equitable, an embodiment allows tracking of total hours a clinician has been assigned to be on-call over the course of a particular time period (e.g., week, month, or year) as well as average hours on-call for similar time periods.

Sometimes on-call staff needs to cover multiple facilities at the same time. An embodiment therefore allows the assignment of clinicians to multiple facilities simultaneously. Additionally, multiple on-call staff may be assigned to a specific group with call preferences (e.g., call clinician A first, if no answer call clinician B, etc.).

A medical staffing office of a given facility, department or care area frequently serves as the hub where all different on-call schedules are sent for distribution. The medical staffing office is likewise often responsible for reviewing the on-call schedule for completeness. This is often done manually. An embodiment enables medical staffing office users to review schedules by getting feedback as to percentage of coverage for a given group, in a given time period. This allows the group to be reviewed with respect to the required or desired coverage, which may be customized.

For example, if a cardiology facility is required to be on-call 24/7/365, any gap would be flagged as <100% coverage. In contrast, if a neurology facility is only contracted to be on-call Monday-Friday, 6 a.m. through 12 a.m., an embodiment automatically ignores gaps in coverage from off hours (in this example from 12 midnight to 6 a.m. and on weekends). Review of past schedules is also supported by an embodiment, allowing for investigative and review processes. For example, an embodiment facilitates auditing, such as to discover what changes were made to an on-call schedule and by whom.

Staff members are ultimately the ones who are on-call and an embodiment addresses their roles as well by providing on-call clinicians with notification of their schedules, for example, by mobile or web-based communication. An embodiment also allows on-call clinicians to input or otherwise provide real time data to the scheduling system, for example, to hand off on-call coverage of their shift to another on-call staff member, to maintain accuracy of the on-call schedule, and also to indicate when the original on-call staff member will be temporarily unavailable, for example if they are currently in surgery or otherwise preoccupied. On-call staff members also may set preferences as to how they want to be contacted and provide multiple phone or pager numbers as well as e-mail addresses, etc.

In an embodiment, the on-call clinician schedule is provided in an electronic format and this electronic on-call scheduling data may be provided in response to user queries, for example, according to a user role. For example, a centralized electronic management system may facilitate the creation, maintenance and updating of an on-call clinician schedule, as well as the providing of the on-call clinician data to a requesting user, even across different applications within a given platform.

By way of non-limiting example, a patient placement and referral system facilitates patient transfers, such as into a new area of care. An embodiment provides on-call clinician data formatted such that a clinician using such a patient placement and referral system may access (e.g., retrieve, receive) current on-call clinician data (e.g., currently on-call clinician, contact information, etc.) such that the clinician user of the patient placement and referral system is able to contact the on-call clinician (e.g., physician) to accelerate the completion of the case and reduce delay a patient experiences during a transition in care.

By integrating the on-call clinician scheduling data with other applications, patient placement and referral system, the users have, within their applications, access to the on-call schedule, thus reducing the switching between applications and also making it easier to log attempts to contact physicians and related information. Similarly, clinicians in other parts of the hospital that have a need to contact an on-call physician at various times have ready access to accurate and current on-call clinician contact information (e.g., a patient experiences paralysis in his or her arm after surgery and a neurologist needs to be called to check for stroke). Having such on-call clinician scheduling data integrated into or accessible to other applications makes the process of performing a task requiring or assisted by an on-call clinician easier.

Having a centralized management system that creates, maintains and provides on-call clinician scheduling data, an embodiment also permits analytics to be performed using the on-call clinician data. For example, healthcare systems spend money paying for clinicians (e.g., physicians) to be on-call. By utilizing the on-call clinician scheduling data, including historical usage data (e.g., tracking of actual calls made to clinician(s) in given time frames) an embodiment can determine utilization of various service lines by time and thus suggest where and when the hospital or facility needs on-call coverage. For instance, if a service line is on-call 24/7/365 but in fact 99% of the time the service line is only paged for an on-call clinician between 6 a.m. and 9 p.m., an embodiment may suggest an adjustment to the on-call clinician schedule on the basis of that data analysis. For example, a user may configure an analysis query for a service line's on-call utilization for a given time period or time frame, specifying an underutilization threshold. Thus, an embodiment may query the historical on-call clinician utilization data to identify one or more times within the time period that the service line has been underutilized per the user's configuration. This permits an embodiment to further identify underutilizations and suggest or implement changes to the on-call clinician schedule.

The illustrated example embodiments will be best understood by reference to the figures. The following description is intended only by way of example, and simply illustrates certain example embodiments.

FIG. 1 illustrates an example on-call clinician scheduling system. In the illustrated example, a centralized electronic management system serves as a data aggregator and facilitates coordinated communications between and among various clinicians, such as medical staff charged with preparing and maintaining an on-call clinician schedule and the on-call clinicians, for example.

The centralized electronic management system may be implemented as a central hub of information. This system therefore permits medical staffing office clinicians to input various data, such as facility on-call scheduling requirements, a list of available on-call clinicians, contact information for the on-call clinicians, scheduling preferences, for example. Likewise, the system has access to various health system databases and proprietary information systems (e.g., real-time location services for tracking assets, patients, etc.).

Thus, in some embodiments the centralized electronic management system may operate as a centralized hub or station for receiving and processing data associated with disclosed methods and techniques, and for generating and sending transmissions associated with disclosed methods and techniques.

In an embodiment, the centralized electronic management system may be implemented with a web interface, such as an interface present at a medical staffing office of health systems (e.g., Health System A, Health System B in FIG. 1) or facilities (e.g., Facility 1, Facility 2, Facility 3, . . . , Facility N, and/or with a mobile interface for clinician mobile devices (e.g., $M_1$, $M_2$, . . . , $M_n$ in FIG. 1). This permits medical staffing office clinicians to access an application (e.g., web hosted application) for creating an initial on-call clinician schedule. The initial on-call clinician schedule may be produced in an automated or semi-automated fashion, i.e., based on a facility's preferences or requirements for on-call clinician coverage, a facility's desire to have equity and balance in the on-call clinician schedule, and/or based on individual clinician's expressed preferences regarding on-call scheduling.

In an embodiment, the system presents the user with input parameters. For example the system may present the user with times for scheduling clinicians on call, and uses the input parameters to automate the process of producing an initial on-call clinician schedule given the data available to the centralized system (e.g., list of clinicians available for on-call scheduling, list of facility requirements, indications of clinician and/or facility preferences, etc.). The digitized scheduling parameters may allow the medical staffing office clinician to guide the creation of the initial on-call clinician schedule that is compiled with the assistance of the system's automation.

Figure 2:
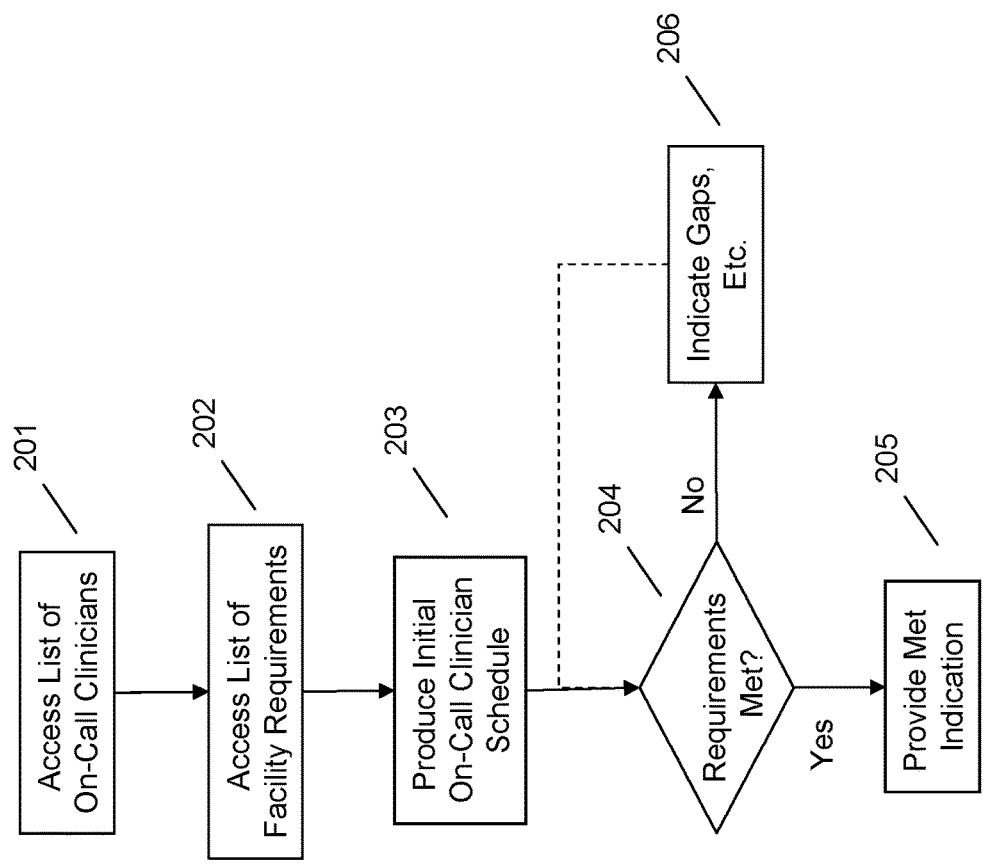
FIG. 2 illustrates an example method of electronic management of on-call clinician scheduling in accordance with disclosed embodiments.

Referring to FIG. 2, by way of example, an embodiment accesses a list of on-call clinicians 201 and a list of requirements for a healthcare facility on-call clinician schedule 202. For example, the system may have data input available that a specific period (e.g., Monday-Friday, 12:00 a.m.-7 a.m.), requires on-call coverage for a facility (e.g., cardiology). Likewise, the system may have access to a list of clinicians that may be scheduled for on-call service during these times, as well as their preferences, availability, and/or unavailability (e.g., prefer no Wednesdays, out of the country this Friday, etc.). These clinician specific preferences, availability and/or unavailability information may be expressed by the clinicians and/or inferred, and thereafter communicated to the system, as further described herein.

Having this data available, an embodiment produces an initial on-call clinician schedule based on the list of on-call clinicians 203. This provides an initial on-call clinician schedule given the input parameters and data available to the system at the time of production. An automated initial on-call schedule is therefore produced for the medical staffing office clinician at 203.

Given the available data (e.g., clinicians available for on-call service, facility requirements, etc.) an embodiment may automatically determine whether the list of requirements is satisfied by the initial on-call clinician schedule 204. By way of example, an embodiment may produce a report or other indication notifying the user (e.g., medical staffing office clinician) if the initial on-call clinician schedule is complete or lacks coverage for certain times. Thus, an embodiment may provide an indication as a result of the determining such that the medical staffing office clinician is apprised immediately of any gaps in coverage. This may take the form of providing a met indication 205 or otherwise notifying the medical staffing office clinician that the initial on-call clinician schedule satisfies all requirements (e.g., facility requirements, clinician preferences, etc.). Otherwise, the system may notify the user that certain requirements have not been met at 206. This may take a variety of forms, for example, depending on how the user has configured the system.

By way of example, a medical staffing office clinician may wish to be notified by the system if there are gaps in coverage, clinician preferences that have not been satisfied, and/or equity requirements have not been achieved (e.g., balance in on-call clinician scheduling). This allows the medical staffing office clinician to be apprised of any issues in completing the on-call clinician schedule in question.

The content of the notification or indication may be configurable and may depend on the nature or quality of data available to the system. By way of example, the system may indicate that certain time periods are not covered in the on-call clinician schedule as well as an associated clinician preference that blocks the gap from being filled. This permits, for example, the medical staffing office clinician to contact the clinician(s) and resolve the situation.

Likewise, the mode of the indication may take a variety of forms and is configurable by the user. For example, the user may be a medical office staffing clinician that is normally in an office setting where an on-screen indication is an appropriate mode of indication. By contrast, a user that tends to be mobile may prefer SMS text notifications, emails or the like as an indication that there is a potential issue with the on-call clinician schedule.

The list of requirements accessed by the system at 201 and/or 202 may include at least one of a clinician scheduling preference, a facility on-call coverage requirement, and a facility scheduling balance preference. This allows the system to determine if at least one of the list of requirements is not satisfied by the initial on-call clinician schedule produced at 203. As a result, the system may automatically generate at least one modification to the initial on-call clinician schedule based on the list of requirements, for example, as part of an iterative processing as illustrated in FIG. 1 with the dashed line.

Referring back to FIG. 1, because the system may be implemented as a centralized data aggregator, an on-call clinician mobile device (e.g., $M_1, M_2, \ldots, M_n$) may provide an update to the on-call clinician schedule. This update may be published as a revised on-call clinician schedule. For example, the publishing of a revision may include updating a database maintaining on-call clinician information (e.g., as part of the centralized electronic management system). This updated information may later be accessed by other users (e.g., medical staffing office clinicians and/or other on call clinicians). Other forms of publication may include for example communicating a message to at least one clinician mobile device (e.g., mobile devices of other on-call clinicians, medical staffing office clinicians, etc.).

In an embodiment, on-call clinician devices are provided with a mobile application that acts as an interface to the centralized electronic management system. This permits the on-call clinicians to provide updates to the system that can in turn be used to update the on-call clinician schedule, even in real-time. For example, an update may include a temporary unavailability notification. A temporary unavailability notification may be provided by an on-call clinician indicating via interfacing with his or her mobile application that he or she is temporarily unavailable. This temporary unavailability notification may be communicated to the system and thus distributed to other users. Likewise, an update may include an unavailability notification, such as an advanced indication from an on-call clinician that he or she is unavailable to be on-call for a given time period or day, for example. In a similar manner, updates may include an unavailability preference and/or availability indications or preferences.

Figure 3:
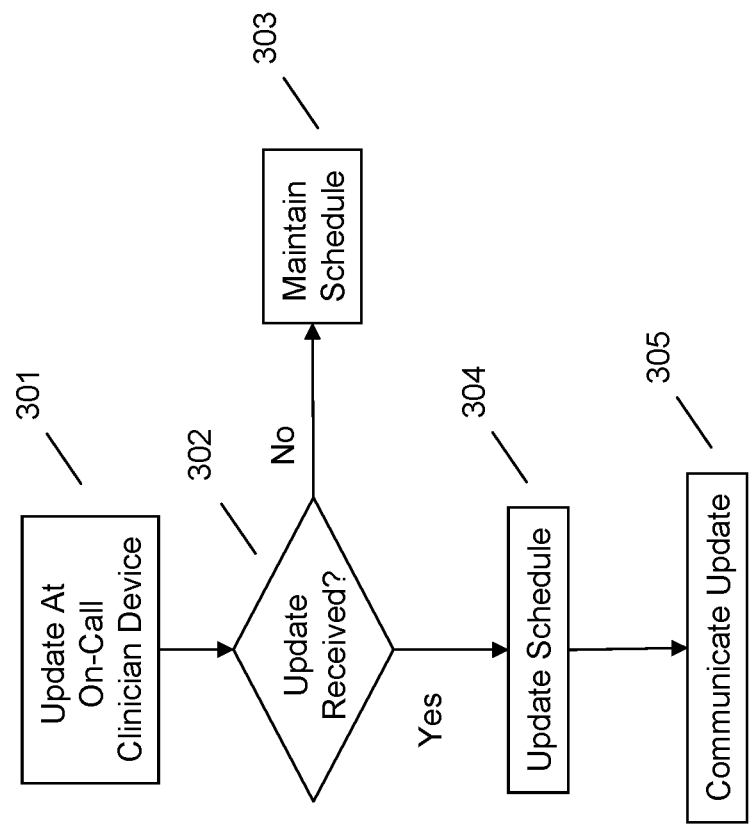
FIG. 3 illustrates an example method of electronic management of on-call clinician schedule updating in accordance with disclosed embodiments.

An example process of updating the on-call clinician schedule is illustrated in FIG. 3. As shown, an on-call clinician device may experience an update event that requires a change to the current on-call clinician schedule at 301. There are a variety of ways in which this might occur.

For example, an on-call clinician may provide a temporary unavailability input at 301, such as by interfacing with his or her mobile application (soft button press, gesture or voice input, etc.). In some embodiments, the update may be inferred, for example, based on device characteristics that are indicative of unavailability. By way of example, a mobile device's accelerometer data, 9-axis sensor data, location (e.g., GPS data, network connectivity data, etc.) or external system data (e.g., near field communication with an RFID tracking system) may provide data that is used to infer an update, such as temporary unavailability, for example. As a specific example, near field or other wireless communication (or lack thereof) between an on-call clinician's mobile device and a network of RFID readers may indicate that an on-call clinician is in an area (e.g., surgical suite) that is indicative of or associated with temporary unavailability. Availability update data may be handled in a similar fashion.

When an update event occurs, the system may determine at 302 if an update has been received from an on-call clinician mobile device. If no update data has been received (which again may be data used to infer an update), the system maintains the on-call clinician schedule at 303. However, if update data has been received, an embodiment update the on-call clinician schedule based on the at least one update at 304. This in turn permits an embodiment to automatically communicate, such as using a wireless communication network, the update to at least one other clinician mobile device at 305.

As described herein, temporary unavailability updates and/or availability updates may be automatically inferred using at least one device characteristic of the on-call clinician mobile device. By way of example, the device characteristic(s) may be selected from the group consisting of a real-time location of the on-call clinician mobile device, orientation data of the on-call clinician mobile device, and accelerometer data of the on-call clinician mobile device.

The centralized system (e.g., as for example illustrated in FIG. 1) may include a database that provides priority clinician information (e.g., associations between different on-call clinicians). For example, priority information may indicate that if clinician A becomes unavailable, clinician B should be contacted. For example, after receiving a temporary unavailability update from a particular clinician at 302 the system may be able to select an on-call clinician mobile device using the priority clinician information, such as for use as a first contact in case an on-call situation arises.

Thus, the updating at 304 may include selecting an alternative on-call clinician for an on-call coverage period based on the priority information. Furthermore, the communicating at 305 may include communicating the update to the on-call clinician mobile device selected using the priority clinician information (e.g., sending a notification that the alternative on-call clinician is now on-call). The notification may be selected from the group consisting of an SMS text message, an email, a page, and an automated voice call As described herein, embodiments represent technical improvements in terms of data coordination, formatting, sharing and organization, particularly with respect to system integration (e.g., medical staffing office scheduling applications and real time location and communication systems) and on-call clinician scheduling and availability monitoring. While various other circuits, circuitry or components may be utilized in information handling devices (also referred to herein as apparatuses, electronic devices, computing devices, mobile devices, or simply devices), with regard to smart phone and/or tablet circuitry 400, an example illustrated in FIG. 4 includes a system on a circuit design found for example in tablet or other mobile computing platforms.

Software and processor(s) are combined in a single circuit 410. Processors comprise internal arithmetic units, registers, cache memory, busses, I/O ports, etc., as is well known in the art. Internal busses and the like depend on different vendors, but essentially all the peripheral devices (420) may attach to a single circuit 410. The circuitry 400 combines the processor, memory control, and I/O controller hub all into a single circuit 410. Also, systems 400 of this type do not typically use SATA or PCI or LPC. Common interfaces, for example, include SDIO and I2C.

There are power management chip(s) 430, such as a battery management unit, BMU, which manage power as supplied, for example, via a rechargeable battery 440, which may be recharged by a connection to a power source (not shown). In at least one design, a single circuit, such as 410, is used to supply BIOS like functionality and DRAM memory.

System 400 typically includes one or more of a WWAN transceiver 450 and a WLAN transceiver 460 for connecting to various networks, such as telecommunications networks and wireless Internet devices (e.g., access points). Additional devices 420 are commonly included. System 400 often includes a touch screen 470 for data input and display/rendering. System 400 also typically includes various memory devices, for example flash memory 480 and SDRAM 490.

Figure 4:
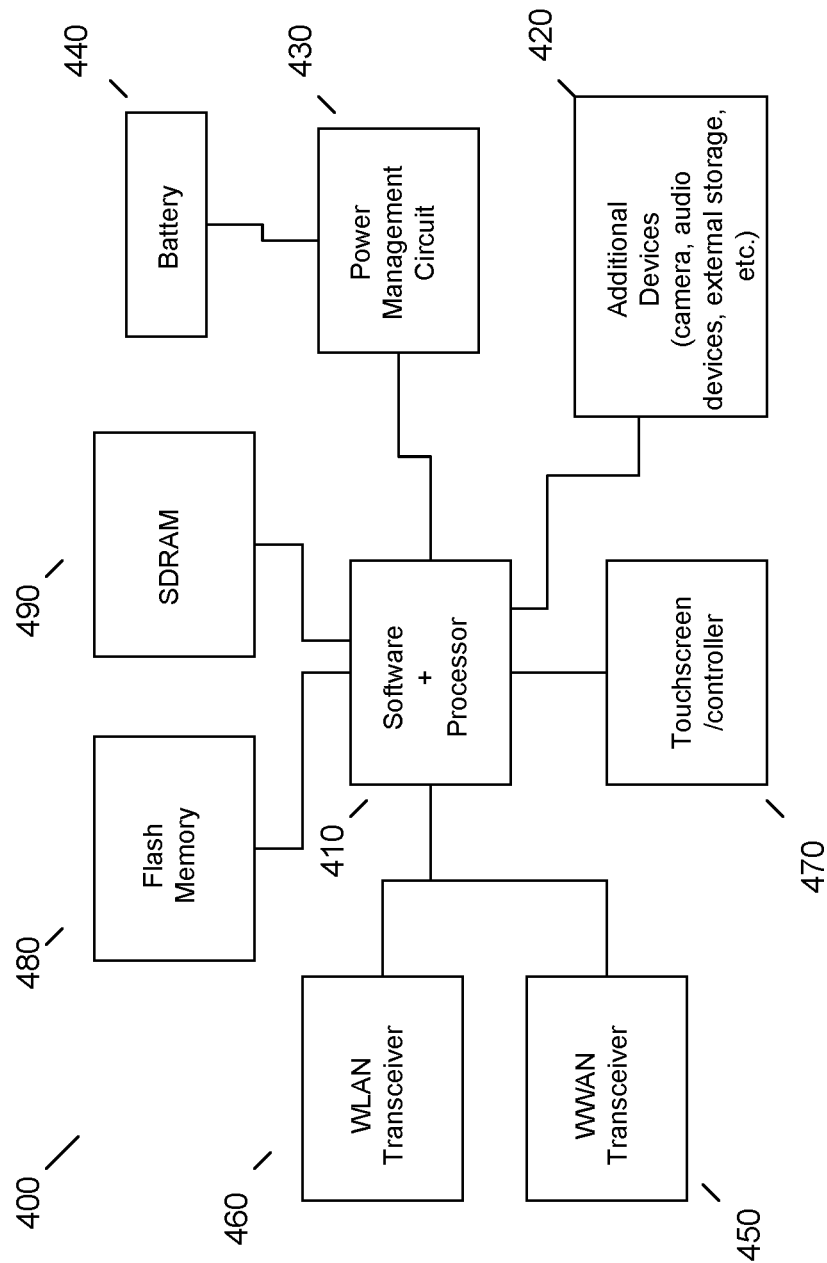
FIG. 4 illustrates example electronic circuitry in accordance with disclosed embodiments.

Circuitry, as for example outlined in FIG. 4, may be used to implement the coordination and management of the various data types described herein. Moreover, the various embodiments regarding mobile applications may be implemented using circuitry such as outlined in FIG. 4. While other types of circuitry may be used, the circuitry outlined in FIG. 4 may also be used to implement a centralized electronic management system as well as other system components, as described herein.

Figure 5:
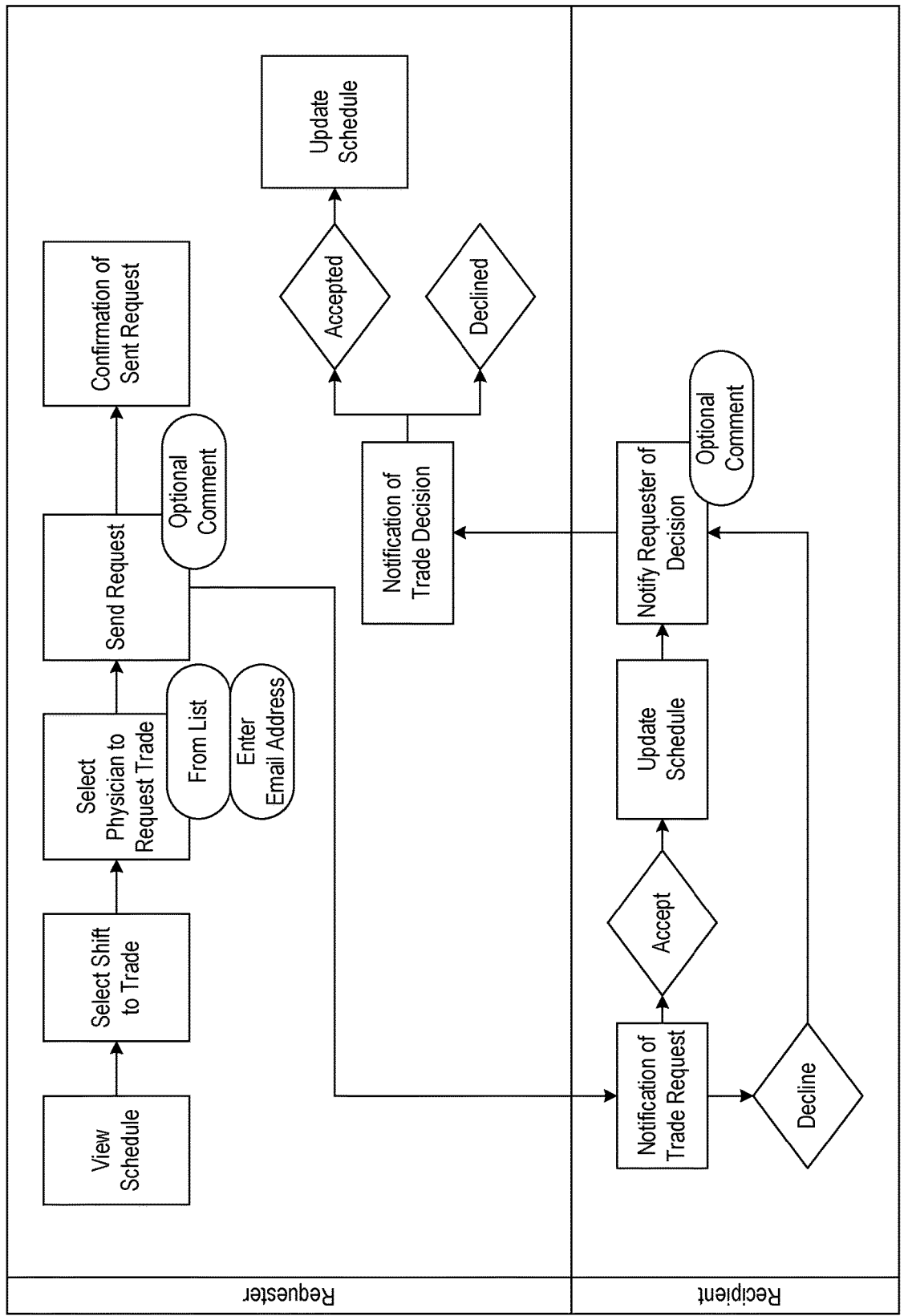
FIG. 5 illustrates a flow chart of an exemplary process for sending a trade request from a requester to a recipient in accordance with disclosed embodiments.

FIG. 5 illustrates a flow chart of an exemplary process for processing partial schedule updates including trade request processing for portions of an individual's schedule. In an embodiment, a requester of a shift trade may view graphical user interface displaying a schedule on a first device, and select a GUI element representing a shift to trade by either selecting from a list or entering an identifier such as an email address. The centralized electronic management system may receive trade request information including an identification of the requestor and/or the electronic device associated with the requestor, an identification of the recipient and/or the electronic device associated with the recipient, and shift data such as a shift time, shift task, department, skill set, and any other relevant information depending on the requirements of the facility. In some embodiments, the centralized electronic management system may process the received trade request information, update one or more databases to reflect the requested trade, and generate an electronic notification to send to the recipient device, including the trade request information. In some embodiments, the trade request information may be transmitted directly from the requesting device to the recipient device, to minimize server loads. In other embodiments, the trade request information may be sent directly from the requesting device to the recipient device, but the requesting device or recipient device may also generate and transmit a notification of the trade request to the centralized electronic management system.

In some embodiments, a trade request with an optional comment may be sent to a second device of a recipient. The requester's first device may receive a confirmation notification of the sent trade request. In some embodiments, the recipient's second device may receive a notification of trade request and provide for display a graphical user interface prompting the requestor to either accept or decline the trade request via one or more response hyperlinks. In some embodiments, the centralized electronic management system may generate and transmit instructions to the recipient's second device to display a graphical user interface having at least the shift data and at least one response hyperlink. Upon the recipient's acceptance of the trade request via selection of an acceptance hyperlink, the centralized electronic management system bay receive acceptance data from the second device generated in response to selection of the acceptance hyperlink. The centralized electronic management system may automatically modify a schedule record in one or more databases associated with the recipient and/or requestor, to indicate acceptance by the recipient, and removal of the shift from the requestor's schedule. The centralized electronic management system may automatically generate and transmit a notification of the decision with an optional comment (either generated by the centralized electronic management system or forwarded by the second device) to the requestor, and the requestor's schedule may be updated. Thereafter, the centralized electronic management system may update at least one database reflecting the trade, and propagate the updated information to linked databases to network-connected databases and systems. In some embodiments, the centralized electronic management system may generate and propagate the update information to the at least one database in real-time or near real-time as the trade request is completed, to provide partial updates rather than transmitting intermittent bulk schedule updates which may spike and strain server and network loads. Upon the recipient's denial of the trade request (such as in response to input selecting a denial hyperlink on the second device), a notification of the decision with an optional comment may be sent to the first device of the requestor. In some embodiments, there may be 1-way and 2-way (bidirectional) communication between the requestor device, the recipient device, the centralized electronic management system, and one or more third party devices regarding the request, discussion, and acceptance data or denial data of trade request with contextual information. In some embodiments, a requester may send a trade request to all physicians that meet the criteria for the trade. The centralized electronic management system may automatically identify the relevant electronic devices associated with the selected physicians, and forward the trade request to the identified electronic devices.

FIG. 6 illustrates an exemplary graphical user interface allowing a user to begin a trading process in accordance with disclosed embodiments. By way of example, Dr. W, the requester, wants to trade his 2 PM shift. He may find the desired shift in his schedule displayed as a list of shifts, and manipulate a graphical user interface element associated with the 2 PM shift. As shown in the example, the user may perform a gesture such as swiping the GUI element for the 2 PM shift to the left, starting the trading process. Upon recognizing the gesture, the centralized electronic management system and/or Dr. W's device may modify the graphical user interface to display a "trade" button next to the GUI element for the shift, allowing Dr. W. to initiate the trade process by selecting the trade button. Thereafter, the displayed graphical user interface may transition to FIG. 7.

Figure 7:
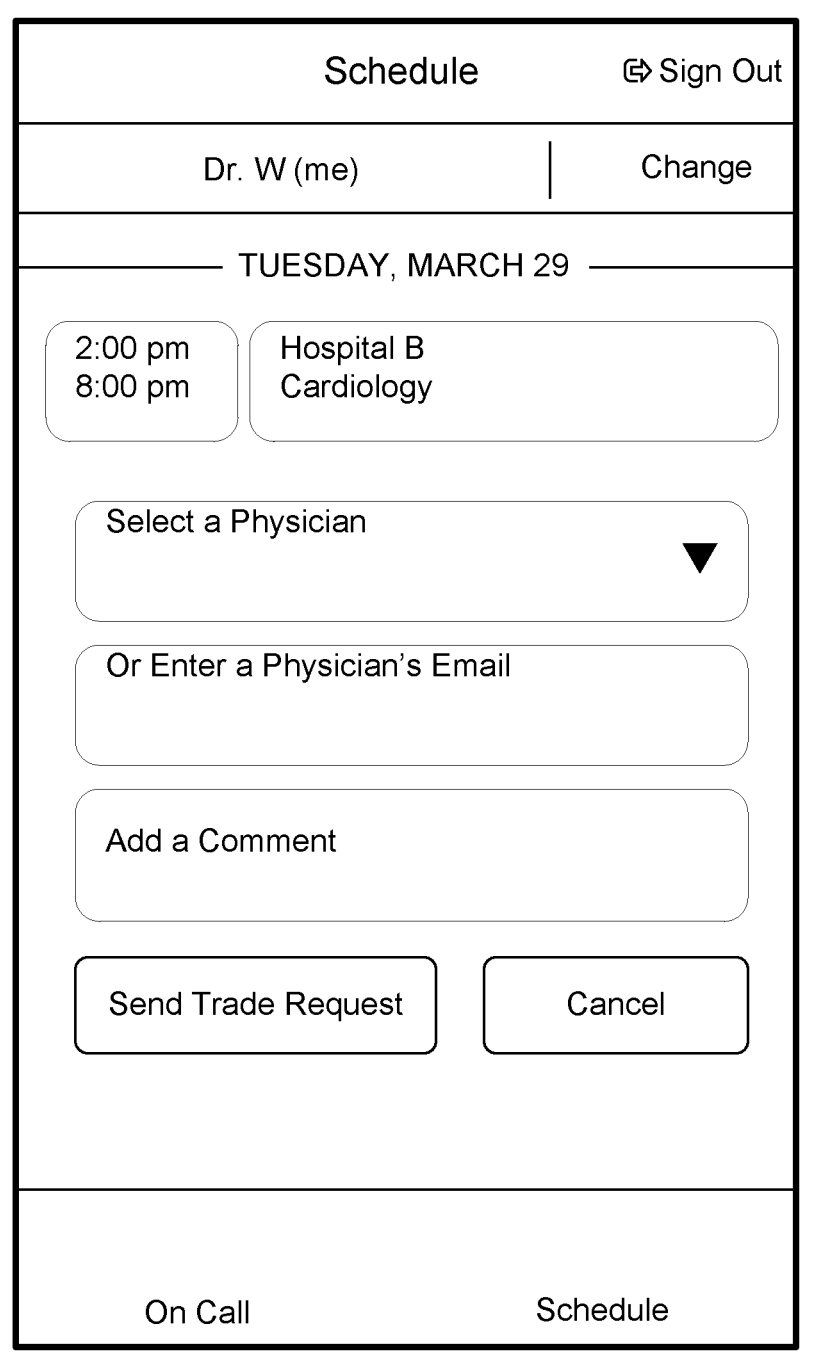

FIG. 7 illustrates an exemplary graphical user interface allowing the user to select a recipient and send a trade request. In some embodiments, Dr. W may select a particular physician to trade the shift with from an existing list within the application or by entering their email address. A menu of physicians may be generated automatically by the centralized electronic management system, by querying one or more databases for information indicative of physician schedules, and by searching the queried information for data indicative of one or more physicians available for the timeframe of the traded shift, and having the proper qualifications. In some embodiments, the graphical user interface may provide a list of all physicians associated with a facility or facility department, and once a recipient is selected from the list or an email is entered, the requester, the graphical user interface may display information to inform Dr. W whether the selected physician is available during the selected time. Dr. W may send the shift trade request, with or without an optional comment. Dr. W's electronic device may receive a confirmation notification and display a graphical user interface element reflecting that the request was sent, and to whom it was sent to.

Figure 8:
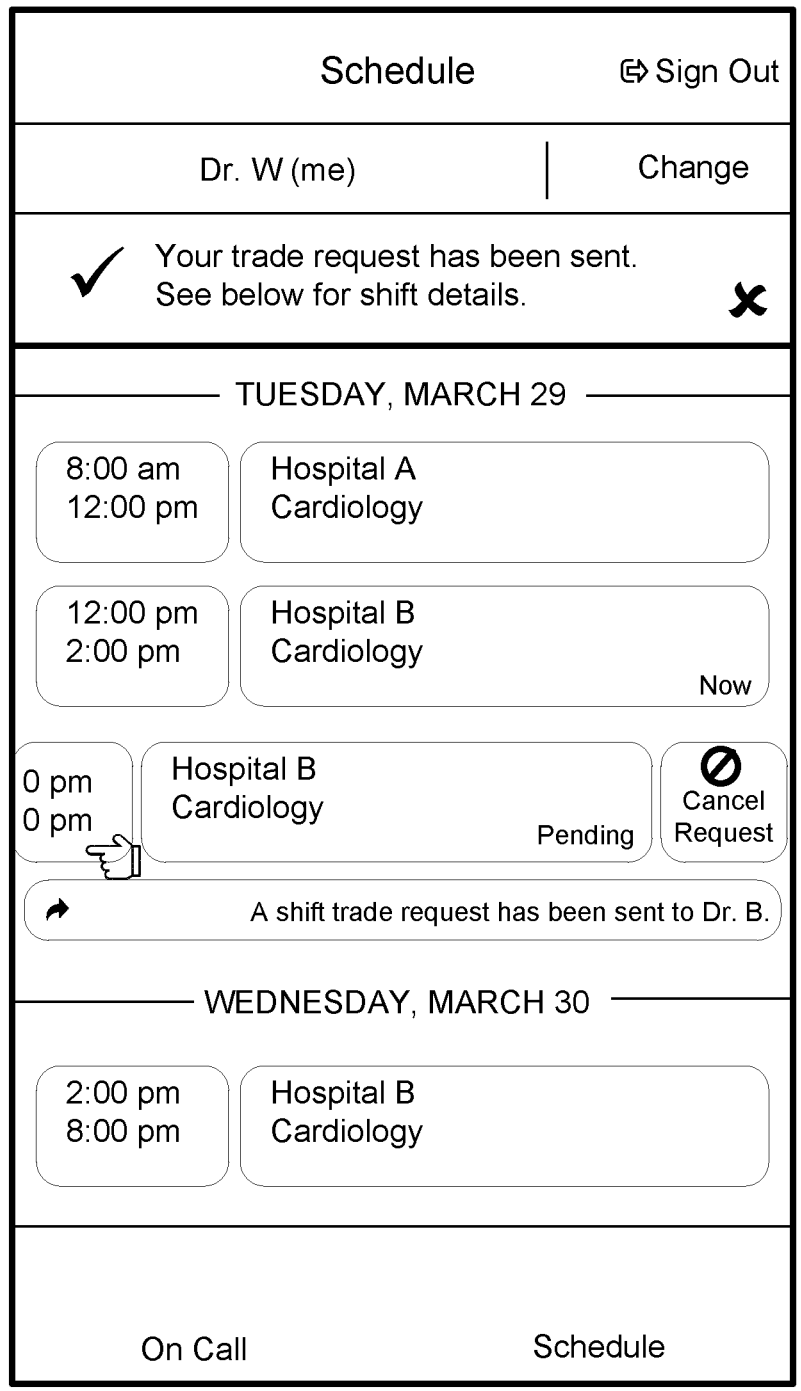
FIG. 8 illustrates an exemplary graphical user interface where a user can cancel a trade request in accordance with disclosed embodiments.

FIG. 8 illustrates an exemplary graphical user interface where a user can cancel a trade request in accordance with disclosed embodiments. By way of example, Dr. W has the option to cancel his request until the shift trade request has been accepted or declined. By manipulating a graphical user interface element associated with the shift, such as by swiping the shift entry to the left, the graphical user interface may display an element which, when selected, may allow Dr. W to cancel the trade request and receive a confirmation that the request has been cancelled.

Figure 9:
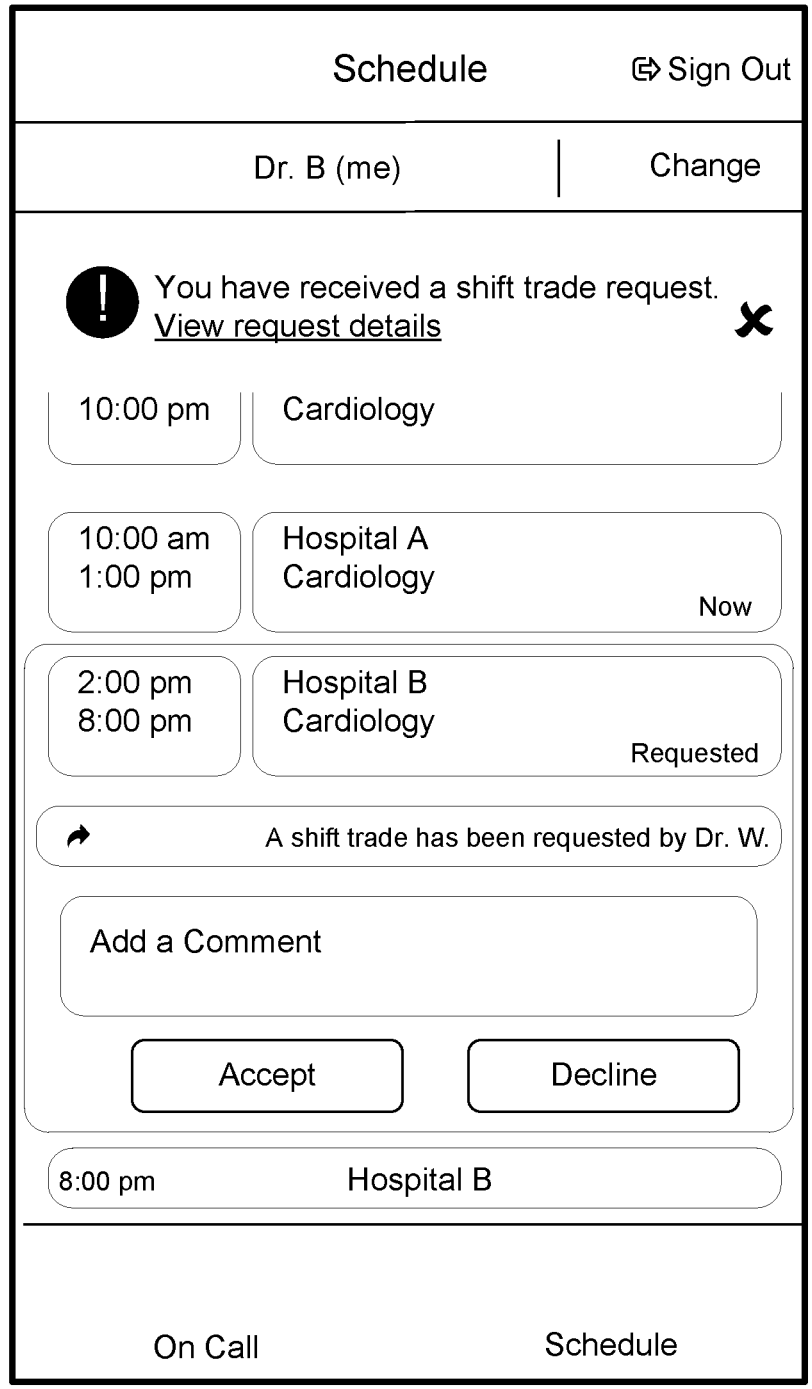
FIG. 9 illustrates an exemplary graphical user interface where a recipient is notified of a trade request in accordance with disclosed embodiments.

FIG. 9 illustrates an exemplary graphical user interface for an electronic device associated with a recipient of a trade request. In some embodiments, trade request recipient Dr. B may be notified that she has received a shift trade request via the graphical user interface displayed on an associated electronic device, as illustrated in FIG. 9. The displayed notification may include a hyperlink which, when selected, may cause the electronic device to provide a new graphical user interface for display, having details about the trade request. The new graphical user interface may inform Dr. B that the trade request was sent by Dr. W, and display the shift entry in the context of Dr. B's schedule. The graphical user interface may include selectable elements such as buttons for accepting or declining the shift trade, with an optional comment if desired. If Dr. B accepts the shift, the schedule is automatically updated and the centralized electronic management system may propagate the updated schedule information for both Dr. W and Dr. B to all associated electronic devices and databases. If Dr. B declines the shift, her schedule remains unchanged, and the centralized electronic management system may propagate only the schedule decline to the requesting electronic device and to other electronic devices associated with the trade request.

Figure 10:
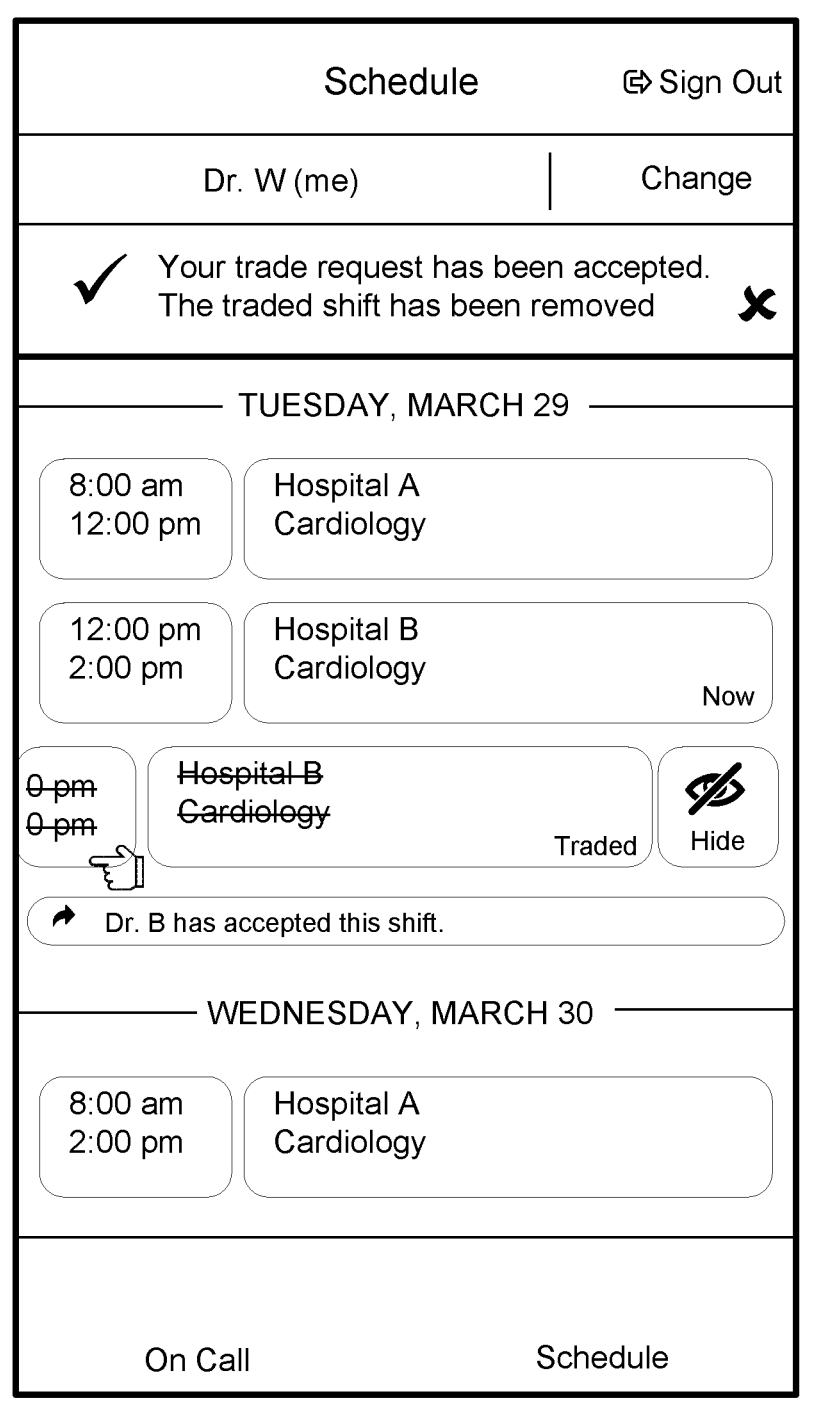

FIG. 10 illustrates an exemplary graphical user interface to a user can view and optionally hide an accepted trade request. By way of example, the graphical user interface may provide a notification to Dr. W that the shift trade request was accepted. The notification may be displayed in response to data propagated from the centralized electronic management system indicating the shift trade and updated schedule information. In some embodiments, the graphical user interface may display the traded shift details with a modified appearance to indicate that the shift is no longer an active shift. In the example shown, the graphical user interface displays the traded shift with a strikethrough-style text to indicate that the shift is traded or otherwise no longer assigned to Dr. W. If Dr. W would no longer like to see this shift on his schedule, he may hide the traded shift by swiping to the left, thereby causing the graphical user interface to display a button which, when selected, may cause the electronic device to modify the graphical user interface to remove the traded shift. In another example, Dr. W may be notified that his shift trade request has been declined, and his schedule my remain unchanged. If the shift trade is declined, Dr. W may begin the trade request process again to send a shift trade request to another physician.

As will be appreciated by one skilled in the art, various aspects may be embodied as a system, method or device program product. Accordingly, aspects may take the form of an entirely hardware embodiment or an embodiment including software that may all generally be referred to herein as a "circuit," "module" or "system." Furthermore, aspects may take the form of a device program product embodied in one or more device readable medium(s) having device readable program code embodied therewith.

It should be noted that the various functions described herein may be implemented using instructions stored on a device readable storage medium such as a non-signal/non-transitory storage device that are executed by a processor. A storage device may be, for example, an electronic, magnetic, optical, electromagnetic, infrared, or semiconductor system, apparatus, or device, or any suitable combination of the foregoing. More specific examples of a storage medium would include the following: a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a storage device is not a signal and "non-transitory" includes all media except signal media.

Program code for carrying out operations may be written in any combination of one or more programming languages. The program code may execute entirely on a single device, partly on a single device, as a stand-alone software package, partly on single device and partly on another device, or entirely on the other device. In some cases, the devices may be connected through any type of connection or network, including a local area network (LAN) or a wide area network (WAN), or the connection may be made through other devices (for example, through the Internet using an Internet Service Provider), through wireless connections, (e.g., near-field communication), or through a hard wire connection, such as over a USB connection.

Example embodiments are described herein with reference to the figures, which illustrate example methods, devices and program products according to various example embodiments. It will be understood that the actions and functionality may be implemented at least in part by program instructions. These program instructions may be provided to a processor of a general purpose information handling device, a special purpose information handling device, or other programmable data processing device to produce a machine, such that the instructions, which execute via a processor of the device implement the functions/acts specified.

It is worth noting that while specific blocks are used in the figures, and a particular ordering of blocks has been illustrated, these are non-limiting examples. In certain contexts, two or more blocks may be combined, a block may be split into two or more blocks, or certain blocks may be re-ordered or re-organized as appropriate, as the explicit illustrated examples are used only for descriptive purposes and are not to be construed as limiting.

As used herein, the singular "a" and "an" may be construed as including the plural "one or more" unless clearly indicated otherwise.

This disclosure has been presented for purposes of illustration and description but is not intended to be exhaustive or limiting. Many modifications and variations will be apparent to those of ordinary skill in the art. The example embodiments were chosen and described in order to explain principles and practical application, and to enable others of ordinary skill in the art to understand the disclosure for various embodiments with various modifications as are suited to the particular use contemplated.

Thus, although illustrative example embodiments have been described herein with reference to the accompanying figures, it is to be understood that this description is not limiting and that various other changes and modifications may be affected therein by one skilled in the art without departing from the scope or spirit of the disclosure.

The invention claimed is:

1. A centralized hospital communication system for detecting partial electronic schedule updates and generating targeted electronic notifications, the system comprising:
    a communication interface configured to establish bidirectional communication with a plurality of electronic devices;
    a centralized electronic management system communicating with a scheduling system comprising schedules for a plurality of individuals scheduled to work within at least one facility, wherein each of the plurality of individuals have stored communication preferences and unavailability and wherein the plurality of individuals are assigned to call groups, each of the call groups corresponding to an entity within the at least one facility and having call preferences identifying hierarchical communication preferences of individuals within the call group;
    a memory storing computer-executable instructions;
    at least one processor configured to execute the stored instructions to:
        receive, via the communication interface at the centralized electronic management system and from a first electronic device associated with an individual, a shift timeframe corresponding to a shift the individual is scheduled to work and wants to trade;
        display, on a graphical user interface at the first electronic device, a list of trade request recipients from a plurality of individuals and comprising other individuals available at the shift timeframe and having qualifications for the shift, wherein the list of trade request recipients are generated in view of real-time unavailability and preferences of the plurality of individuals and are displayed based upon the hierarchical communication preferences of the plurality of individuals, wherein the real-time unavailability is identified based upon correlating unavailability preferences of each of the plurality of individuals with information regarding the shift timeframe to identify those individuals from the plurality of individuals that are unavailable at the shift timeframe and based upon identifying characteristics of devices for each of the plurality of individuals indicative of a real-time unavailability from at least one of accelerometer data, 9-axis sensor data, and location data;
        receive, via the communication interface and from the individual via the first electronic device, a trade request, the trade request comprising (i) an identification of a requestor corresponding to the individual, (ii) an identification of a trade request recipient from the list of trade request recipients and selected by the individual within the graphical user interface, and (iii) shift data, wherein the shift data comprises the shift timeframe and at least one of a shift task, department, and skill set;
        generate and transmit a request electronic notification to a second electronic device associated with the request recipient included in the trade request information, the request electronic notification providing a notification to the request recipient of the trade request and providing input areas for accepting the trade request and declining the trade request;
        receive, from the second electronic device, acceptance data generated in response to selection of the input area for accepting the trade request;
        automatically modify, within a central database and the scheduling system, a first electronic schedule record associated with the recipient to reflect a new schedule of the recipient and a second electronic schedule record associated with the requestor to reflect a new schedule of the requestor based on the acceptance data;
        automatically update the schedules within the scheduling system reflecting the modified first electronic schedule record and the modified second electronic schedule record;
        receive, from the patient placement and referral system, a request to contact a current on-call individual; and
        provide, to another electronic device associated with a user of the patient placement and referral system, updated on-call individual information identified from the updated schedules, wherein the updated on-call individual information is provided in real-time and is based upon the hierarchical communication preferences of individuals within the call group associated with the on-call individual, wherein the updated on-call individual information comprises priority information identifying an alternative on-call individual provided responsive to identifying the recipient is unavailable at the time of the user requesting on-call individual information, wherein identifying the recipient is unavailable is based upon real-time data provided by the recipient to the scheduling system identifying the unavailability and wherein the alternative on-call individual is identified based upon the hierarchical communication preferences of individuals within the call group of the recipient.

2. The centralized communication system of claim 1, wherein the first electronic device is associated with a first clinician, the second electronic device is associated with a second clinician, and the shift data is associated with a clinician shift at a hospital.

3. The centralized communication system of claim 1, wherein at least one of the first electronic device and the second electronic device is a mobile device.

4. The centralized communication system of claim 1, wherein the automatically updating comprises modifying an appearance of a graphical user interface of the first electronic device to indicate that a shift associated with the shift data is no longer associated with the requestor.

5. The centralized communication system of claim 1, wherein the automatically updating comprises modifying an appearance of a graphical user interface of the second electronic device to indicate that a shift associated with the shift data is associated with the request recipient.

6. The system of claim 1, wherein the update is generated and propagated in near real-time as the trade request is completed.

7. A non-transitory computer readable medium storing instructions which, when executed, configure at least one processor to perform computerized operations for detecting partial electronic schedule updates and generating targeted electronic notifications for a hospital, the operations comprising:
receiving, via a communication interface at a centralized electronic management system and from a first electronic device associated with an individual, a shift timeframe corresponding to a shift the individual is scheduled to work and wants to trade, the centralized electronic management system communicating with a scheduling system comprising schedules for a plurality of individuals scheduled to work within at least one facility, wherein each of the plurality of individuals have stored communication preferences and unavailability and wherein the plurality of individuals are assigned to call groups, each of the call groups corresponding to an entity within the at least one facility and having call preferences identifying hierarchical communication preferences of individuals within the call group;
displaying, on a graphical user interface at the first electronic device, a list of trade request recipients from a plurality of individuals and comprising other individuals available at the shift timeframe and having qualifications for the shift, wherein the list of trade request recipients are generated in view of real-time unavailability and preferences of the plurality of individuals and are displayed based upon the hierarchical communication preferences of the plurality of individuals, wherein the real-time unavailability is identified based upon correlating unavailability preferences of each of the plurality of individuals with information regarding the shift timeframe to identify those individuals from the plurality of individuals that are unavailable at the shift timeframe and based upon identifying characteristics of devices for each of the plurality of individuals indicative of a real-time unavailability from at least one of accelerometer data, 9-axis sensor data, and location data;
receiving, via the communication interface and from the individual via the first electronic device, a trade request, the trade request comprising (i) an identification of a requestor corresponding to the individual, (ii) an identification of a trade request recipient from the list of trade request recipients and selected by the individual within the graphical user interface, and (iii) shift data, wherein the shift data comprises the shift timeframe and at least one of a shift task, department, and skill set;
generating and transmitting a request electronic notification to a second electronic device associated with the request recipient included in the trade request information, the request electronic notification providing a notification to the request recipient of the trade request and providing input areas for accepting the trade request and declining the trade request;
receiving, from the second electronic device, acceptance data generated in response to selection of the input area for accepting the trade request;
automatically modifying, within a central database and the scheduling system, a first electronic schedule record associated with the recipient to reflect a new schedule of the recipient and a second electronic schedule record associated with the requestor to reflect a new schedule of the requestor based on the acceptance data;
automatically updating the schedules within the scheduling system reflecting the modified first electronic schedule record and the modified second electronic schedule record;
receiving, from the patient placement and referral system, a request to contact a current on-call individual; and
providing, to another electronic device associated with a user of the patient placement and referral system, updated on-call individual information identified from the updated schedules, wherein the updated on-call individual information is provided in real-time and is based upon the hierarchical communication preferences of individuals within the call group associated with the on-call individual, wherein the updated on-call individual information comprises priority information identifying an alternative on-call individual provided responsive to identifying the recipient is unavailable at the time of the user requesting on-call individual information, wherein identifying the recipient is unavailable is based upon real-time data provided by the recipient to the scheduling system identifying the unavailability and wherein the alternative on-call individual is identified based upon the hierarchical communication preferences of individuals within the call group of the recipient.

8. The non-transitory computer readable medium of claim 7, wherein the first electronic device is associated with a first clinician, the second electronic device is associated with a second clinician, and the shift data is associated with a clinician shift at a hospital.

9. The non-transitory computer readable medium of claim 7, wherein at least one of the first electronic device and the second electronic device is a mobile device.

10. The non-transitory computer readable medium of claim 7, wherein the automatically updating comprises modifying an appearance of a graphical user interface of the first electronic device to indicate that a shift associated with the shift data is no longer associated with the requestor.

11. The non-transitory computer readable medium of claim 7, wherein the automatically updating comprises modifying an appearance of a graphical user interface of the second electronic device to indicate that a shift associated with the shift data is associated with the request recipient.

12. The non-transitory computer readable medium of claim 7, wherein the update is generated and propagated in near real-time as the trade request is completed.

13. A computerized method for detecting partial electronic schedule updates and generating targeted electronic notifications using a centralized hospital communication system, the method comprising:

receiving, via a communication interface at a centralized electronic management system and from a first electronic device associated with an individual, a shift timeframe corresponding to a shift the individual is scheduled to work and wants to trade, the centralized electronic management system communicating with a scheduling system comprising schedules for a plurality of individuals scheduled to work within at least one facility, wherein each of the plurality of individuals have stored communication preferences and unavailability and wherein the plurality of individuals are assigned to call groups, each of the call groups corresponding to an entity within the at least one facility and having call preferences identifying hierarchical communication preferences of individuals within the call group;

displaying, on a graphical user interface at the first electronic device, a list of trade request recipients from a plurality of individuals and comprising other individuals available at the shift timeframe and having qualifications for the shift, wherein the list of trade request recipients are generated in view of real-time unavailability and preferences of the plurality of individuals and are displayed based upon the hierarchical communication preferences of the plurality of individuals, wherein the real-time unavailability is identified based upon correlating unavailability preferences of each of the plurality of individuals with information regarding the shift timeframe to identify those individuals from the plurality of individuals that are unavailable at the shift timeframe and based upon identifying characteristics of devices for each of the plurality of individuals indicative of a real-time unavailability from at least one of accelerometer data, 9-axis sensor data, and location data;

receiving, by at least one processor via a communication interface and from the individual via the first electronic device, a trade request, the trade request comprising (i) an identification of a requestor corresponding to the individual, (ii) an identification of a trade request recipient from the list of trade request recipients and selected by the individual within the graphical user interface, and (iii) shift data, wherein the shift data comprises the shift timeframe and at least one of a shift task, department, and skill set;

generating and transmitting a request electronic notification to a second electronic device associated with the request recipient included in the trade request information, the request electronic notification providing a notification to the request recipient of the trade request and providing input areas for accepting the trade request and declining the trade request;

receiving, from the second electronic device, acceptance data generated in response to selection of the input area for accepting the trade request;

automatically modifying, within a central database and the scheduling system, a first electronic schedule record associated with the recipient to reflect a new schedule of the recipient and a second electronic schedule record associated with the requestor to reflect a new schedule of the requestor based on the acceptance data;

automatically updating the schedules within the scheduling system reflecting the modified first electronic schedule record and the modified second electronic schedule record, wherein the one or more linked networked databases tracks a total number and average number of on-call hours for each of the plurality of individuals and wherein the total number and average number of on-call hours are searchable and filterable by a provided time period; and receiving, from the patient placement and referral system, a request to contact a current on-call individual; and providing, to another electronic device associated with a user of the patient placement and referral system, updated on-call individual information identified from the updated schedules, wherein the updated on-call individual information is provided in real-time and is based upon the hierarchical communication preferences of individuals within the call group associated with the on-call individual, wherein the updated on-call individual information comprises priority information identifying an alternative on-call individual provided responsive to identifying the recipient is unavailable at the time of the user requesting on-call individual information, wherein identifying the recipient is unavailable is based upon real-time data provided by the recipient to the scheduling system identifying the unavailability and wherein the alternative on-call individual is identified based upon the hierarchical communication preferences of individuals within the call group of the recipient.

14. The method of claim 13, wherein the first electronic device is associated with a first clinician, the second electronic device is associated with a second clinician, and the shift data is associated with a clinician shift at a hospital.

15. The method of claim 13, wherein at least one of the first electronic device and the second electronic device is a mobile device.

16. The method of claim 13, wherein the automatically updating comprises modifying an appearance of a graphical user interface of the first electronic device to indicate that a shift associated with the shift data is no longer associated with the requestor.

17. The method of claim 13, wherein the automatically updating comprises modifying an appearance of a graphical user interface of the second electronic device to indicate that a shift associated with the shift data is associated with the request recipient.

18. The method of claim 13, wherein the update is generated and propagated in near real-time as the trade request is completed.

* * * * *